US00PP36229P2

(12) United States Plant Patent
Kolster et al.

(10) Patent No.: US PP36,229 P2
(45) Date of Patent: Oct. 29, 2024

(54) ***HYDRANGEA* PLANT NAMED 'Hokomadraq'**

(50) Latin Name: *Hydrangea macrophylla*
Varietal Denomination: Hokomadraq

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 18/497,869

(22) Filed: Oct. 30, 2023

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of *Hydrangea macrophylla* plant named 'Hokomadraq' that is characterized by its compact, densely branched and rounded plant habit, its inflorescences with sterile sepals that are red-pink in color, its mophead inflorescences with sterile flowers with a sturdy texture (hard), and its suitability as a potted plant and for cut flowers.

3 Drawing Sheets

Botanical classification: *Hydrangea macrophylla.*
Varietal denomination: 'Hokomadraq'.

BACKGROUND OF THE INVENTION

The present invention relates to a new and distinct cultivar of *Hydrangea macrophylla* and will be referred to hereafter by its cultivar name, 'Hokomadraq'. 'Hokomadraq' represents a new bigleaf hydrangea, a perennial shrub grown for use in the landscape, as a potted plant, and as a cut flower.

'Hokomadraq' derived from an ongoing controlled breeding program directed by the Inventors. The goal of the breeding program included developing a new cultivar of *Hydrangea* with hard (sturdy) textured flowers with dark pink to red-pink color inflorescences and suitability as a potted plant and as a cut flower.

'Hokomadraq' arose from a controlled cross made by the Inventors in Boskoop, The Netherlands in May of 2010 between an unnamed and unpatented proprietary plant in the Inventor's breeding program, reference no. 08-007-02, as the female parent and 'Kolmaru' (U.S. Plant Pat. No. 25,104) as the male parent. The new cultivar was selected as a single unique plant in May of 2012 from the resulting seedling from the above cross.

Asexual propagation of the new cultivar was first accomplished by stem cuttings under the direction of the Inventors in July of 2012 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomadraq' as a unique cultivar of *Hydrangea macrophylla.*

1. 'Hokomadraq' exhibits a compact, densely branched and rounded plant habit.
2. 'Hokomadraq' exhibits inflorescences with sterile sepals that are red-pink in color.
3. 'Hokomadraq' exhibits mophead inflorescences with sterile flowers with a sturdy texture (hard).
4. 'Hokomadraq' exhibits suitability as a potted plant and for cut flowers.

The female parent of 'Hokomadraq' differs from 'Hokomadraq' in having inflorescences with sterile sepals that are pink color, shorter branches, and darker green leaves. The male parent of 'Hokomadraq' differs from 'Hokomadraq' in having leaves that are smaller and darker green in color and inflorescences that are rounder in shape. 'Hokomadraq' can be most closely compared to the *Hydrangea macrophylla* cultivars 'Hortmadace' (U.S. Plant Pat. No. 28,084) and 'Hortmalegretto' (U.S. Plant Pat. No. 30,045). 'Hortmadace' and 'Hortmalegretto' are both similar to 'Hokomadraq' in having red-pink color inflorescences and suitability for use as cut flowers. 'Hortmadace' differs from 'Hokomadraq' in having inflorescences that are more intense in color, leaves that are slightly darker green in color, sterile sepal margins that are serrate, and inflorescences that are rounder in shape. 'Hortmalegretto' differs from 'Hokomadraq' in having inflorescences that are more intense in color, sterile sepal margins that are dentate, and flower margins and leaves margins that are dentate.

BRIEF DESCRIPTION OF THE DRAWINGS

The accompanying color photographs illustrate the overall appearance and distinct characteristics of the new

*Hydrangea*. The photographs were taken of plants 1.5 years in age as grown outdoors in 2-gallon containers in Abbotsford, BC, Canada.

Figure 1:
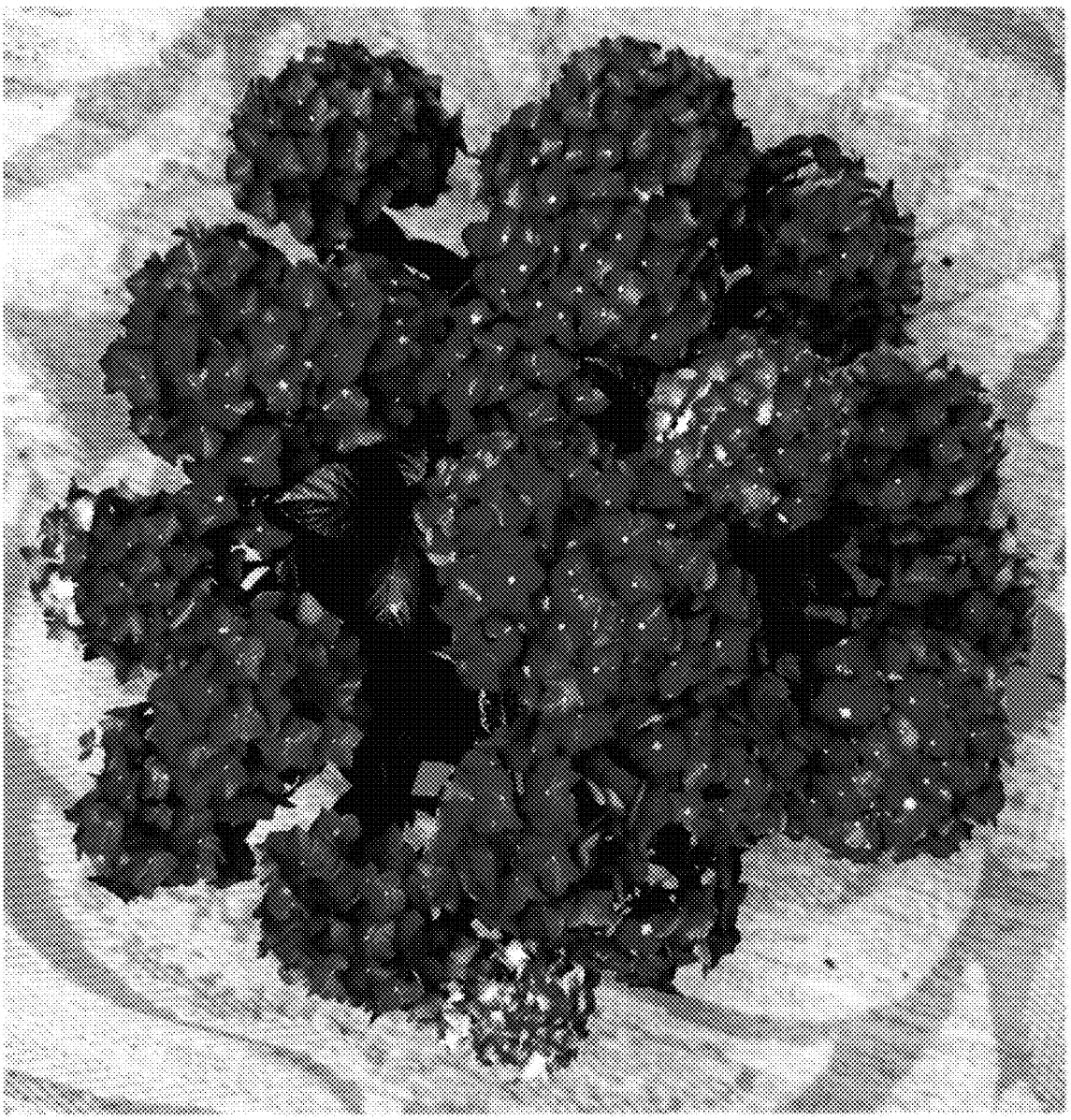

The photograph in FIG. 1 provides a top view of 'Hokomadraq' in bloom.

Figure 2:
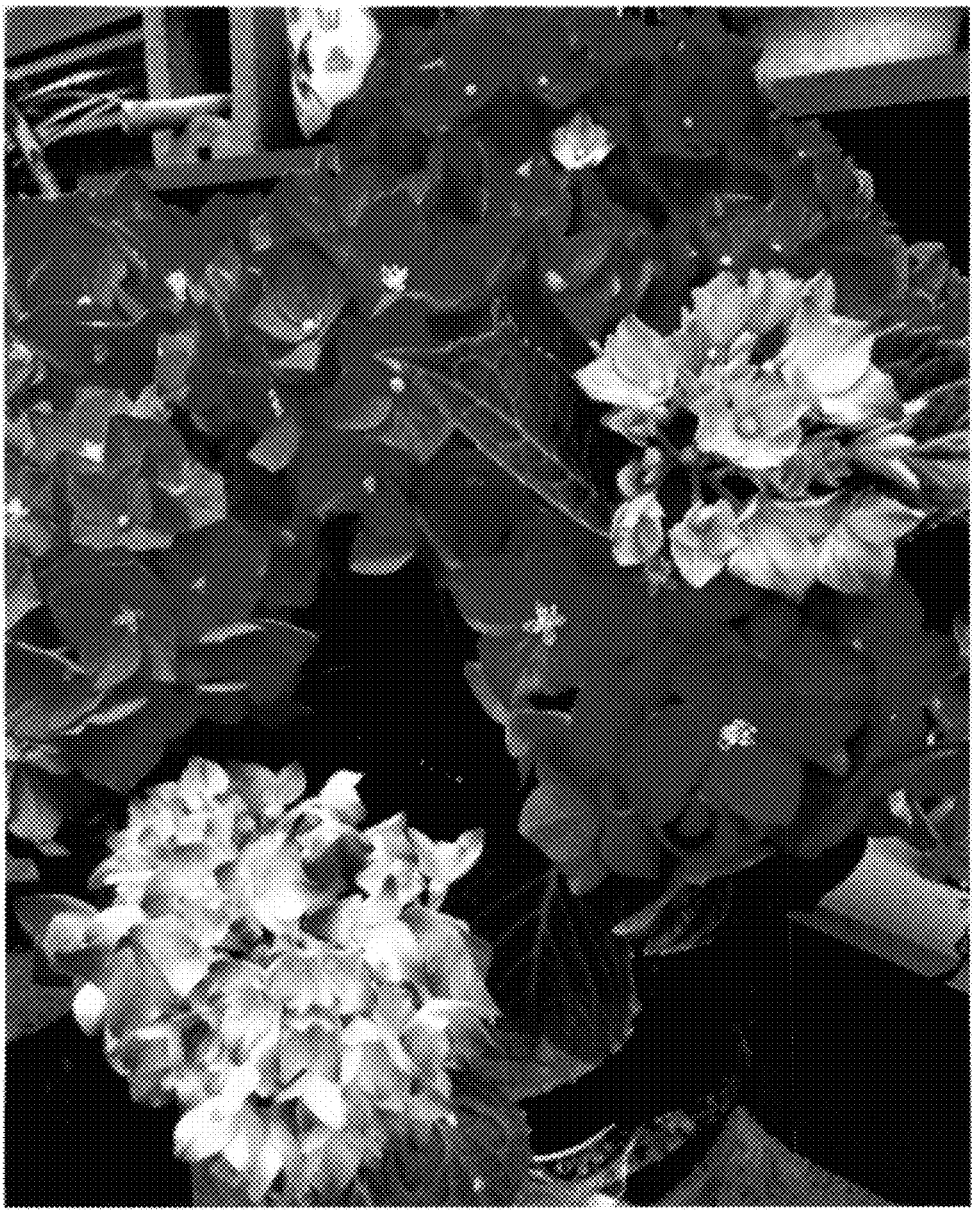

The photograph in FIG. 2 provides a close-up view of the inflorescences of 'Hokomadraq'.

Figure 3:
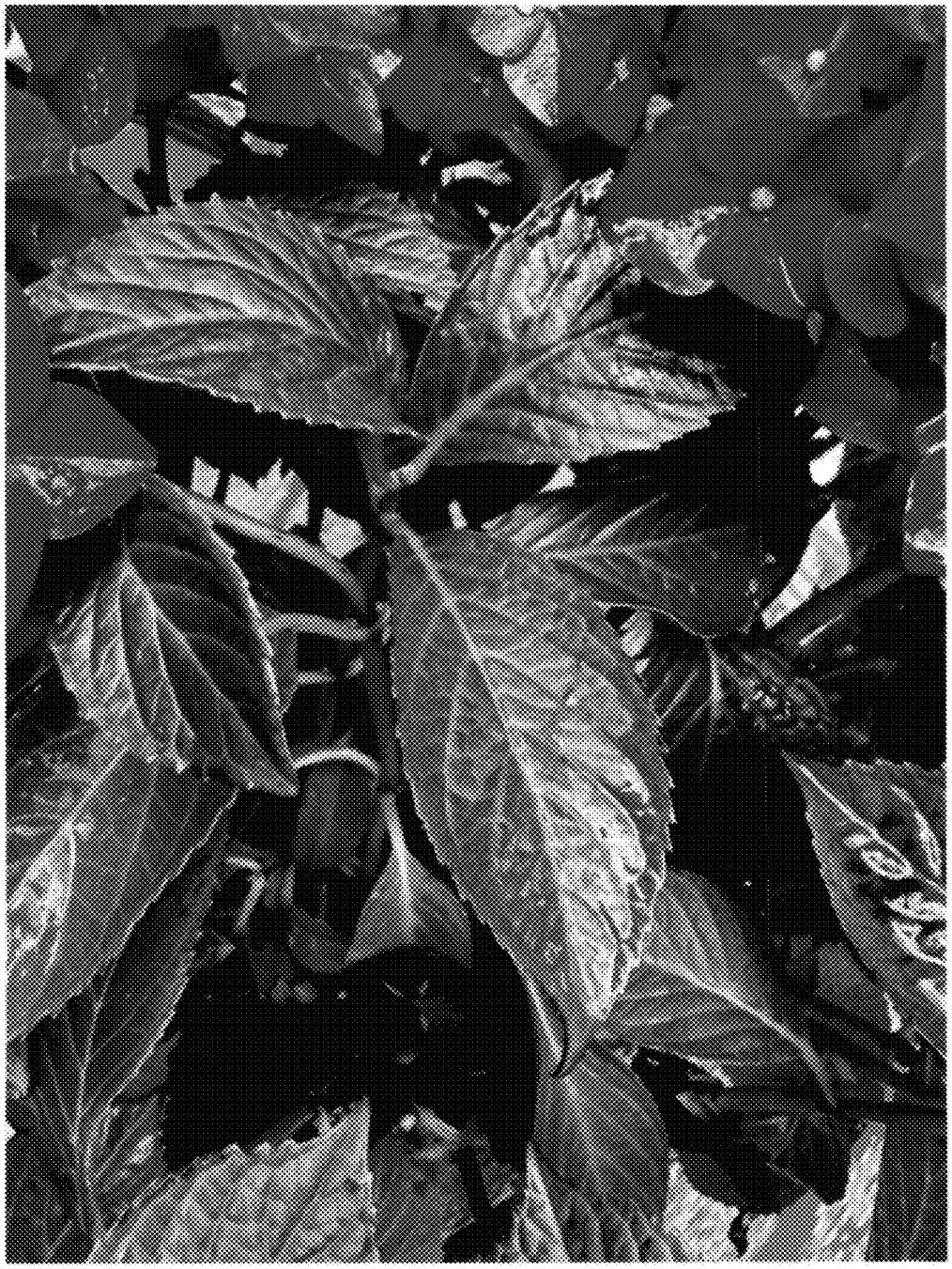

The photograph in FIG. 3 provides a close-up view of the foliage of 'Hokomadraq'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a description of 1.5-year-old plants of 'Hokomadraq' as grown outdoors in 2-gallon containers in Abbotsford, BC, Canada. The plants were grown under non-bluing conditions. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring to summer in The Netherlands with flowers showy at least for 2 months.

*Plant type*.—Deciduous shrub, mophead type *Hydrangea*.

*Plant habit*.—Compact, densely branched, rounded.

*Height and spread*.—Reaches 40 cm in in height and 51 cm in width as a 1.5-year-old plant grown in a container and 1 m in height and spread as grown in the landscape.

*Hardiness*.—At least in U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 6 weeks for root initiation with a young rooted plant produced in an average of 18 weeks.

*Growth rate and vigor*.—Moderate.

Branch description:

*Branch shape*.—Round to flattened oval.

*Branch strength*.—Main; strong, lateral; moderately strong and bendable.

*Branch color*.—Young and mature; 144B in color, flushed at the base with 200A, moderately covered in narrow lenticels, 1.5 mm in length, 166A in color, woody branches; N199A and 200B.

*Branch size*.—Main branches; an average of 16 cm in length, 1 cm in diameter, lateral branches; average of 20 cm in length and 3 mm in diameter.

*Branch surface*.—Young and mature; glossy, glabrous, older branches; woody, rugose, matte, dry.

*Branch aspect*.—Upright to outward.

*Internode length*.—An average of 6 cm.

*Branching*.—Densely branched; 14 main branches, up to 8 lateral branches per main branch.

Foliage description:

*Leaf shape*.—Ovate.

*Leaf arrangement*.—Opposite.

*Leaf division*.—Simple.

*Leaf base*.—Acute.

*Leaf apex*.—Acuminate.

*Leaf margins*.—Serrate.

*Leaf venation*.—Pinnate, upper surface color 145A, lower surface not distinguishable, main vein 145C in color.

*Leaf size*.—An average of 8.5 cm in length and 4 cm in width.

*Leaf attachment*.—Petiolate.

*Leaf number*.—An average of 10 per lateral stem.

*Leaf surface*.—Young and mature; both surfaces glabrous, lower surface matte, upper surface leathery with a slight sheen.

*Leaf color*.—Upper surface; 146A, lower surface; 146B.

*Petioles*.—An average of 1 cm in length and 2 mm in width, both surfaces are smooth and slightly glossy and 145A in color.

Inflorescence description:

*Inflorescence type*.—Terminal panicle, rounded mophead comprised of a sterile flowers above fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 7 cm in height and 11 cm in diameter.

*Flower number*.—Per mophead; an average of 40 sterile flowers and 10 fertile flowers.

*Flower fragrance*.—None.

*Flower aspect*.—Upright to slightly nodding.

*Flower size*.—Sterile flowers; an average of 4 cm in diameter and 1 cm in depth, fertile flowers; an average of 5 mm in diameter and 3 mm in depth.

*Flower type*.—Rotate.

*Peduncles*.—Strong, bendable, round in shape, an average of 1.5 cm in length and 3 mm in diameter, glossy, glabrous, color: young and mature 144C, flushed at the base with 200A, moderately covered in narrow lenticels, 1.5 mm in length, 166A in color.

*Pedicels*.—Sterile flowers; moderately strong, bendable, round in shape, an average of 1 cm in length and 2 mm in diameter, matte and satiny surface, color; 144B, flushed with 200A at the base, fertile flowers; moderately strong, bendable, round in shape, an average of 1 mm in length and 0.5 mm in diameter, matte and satiny surface.

*Petals*.—Sterile flowers: petal spot; 1 mm in depth, 3 mm in diameter, flattened and round in shape, color; when young 145C, mature 62C, when petals open; are 3 mm in length, 1 mm in width, narrow in shape, cuneate base, acute apex, both surfaces velvety, glabrous and matte, color; both surfaces 63C, margins 62D, fertile flowers: 3 mm in diameter, 1 mm in depth, round in shape, color; when young 145C, mature 62C, petals drop at maturity.

*Sepals*.—Sterile flowers; 4, rotate and slightly overlapping, apex slightly emarginate to obtuse, base is squared, margins are slightly undulate, deltoid, an average of 2 cm in length and 1.5 cm in width (at the widest point), both surfaces glabrous, velvety and matte, thin, color: when opening upper and lower surface; 145C, becoming flushed with 63B at the tips, when sepals are fully open upper surface; 63A and 63B, when sepals are fully open low surface; 63B and 63C, fertile flowers; 5, fused base, apex is acute, an average of 1 mm in length and 1 mm in width (at the widest point), both surfaces glabrous and 158A in color.

Reproductive organs:

*Gynoecium*.—Sterile flowers; 2 pistils, an average of 2 mm in length, stigma; club-shaped, bifid, and N155A in color, style; 0.7 mm in length, N155A in color, ovary is superior, 2 mm in depth, 1 mm in diameter, N155A in color, fertile flowers; 2 pistils, an average of 3 mm in length, stigma; club-shaped, bifid, and N155A in color, style; 1 mm in length, N155A in color, ovary is superior, 2 mm in depth, 1 mm in diameter, and N155A in color.

*Androecium*.—Sterile flowers; an average of 8 stamens, filaments; an average of 2 mm in length, 0.4 mm in diameter, and NN155D in color, anthers; oval in shape, an average of 0.7 mm in width, 0.5 mm in depth, 155A in color, fading to 202A, pollen; low in quantity, 158A in color, fertile flowers; an average of 15 stamens, filaments; an average of 1 mm in length, 0.4 mm in diameter, and 159A in color, anthers; oval in shape, an average of 0.7 mm in width, 0.5 in depth, 155A in color, fading to 202A, pollen; moderate in quantity, 155A in color.

*Fruit and seed*.—None observed to date.

It is claimed:

1. A new and distinct cultivar of *Hydrangea* plant named 'Hokomadraq' substantially as herein illustrated and described.

* * * * *